(12) United States Patent
Chomet et al.

(10) Patent No.: US 9,121,028 B2
(45) Date of Patent: Sep. 1, 2015

(54) SELECTIVE GENE EXPRESSION IN PLANTS

(75) Inventors: Paul S. Chomet, Mystic, CT (US); Michael D. Edgerton, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 890 days.

(21) Appl. No.: 11/518,571

(22) Filed: Sep. 8, 2006

(65) Prior Publication Data

US 2007/0061922 A1 Mar. 15, 2007

Related U.S. Application Data

(60) Provisional application No. 60/715,632, filed on Sep. 9, 2005.

(51) Int. Cl.
*C12N 15/113* (2010.01)
*C12N 15/82* (2006.01)

(52) U.S. Cl.
CPC ........ *C12N 15/8216* (2013.01); *C12N 15/8218* (2013.01)

(58) Field of Classification Search
None
See application file for complete search history.

(56) References Cited

U.S. PATENT DOCUMENTS

| | | |
|---|---|---|
| 4,959,317 A | 9/1990 | Sauer |
| 5,004,863 A | 4/1991 | Umbeck |
| 5,015,580 A | 5/1991 | Christou et al. |
| 5,159,135 A | 10/1992 | Umbeck |
| 5,416,011 A | 5/1995 | Hinchee et al. |
| 5,463,174 A | 10/1995 | Moloney et al. |
| 5,518,908 A | 5/1996 | Corbin et al. |
| 5,527,695 A | 6/1996 | Hodges et al. |
| 5,538,880 A | 7/1996 | Lundquist et al. |
| 5,550,318 A | 8/1996 | Adams et al. |
| 5,569,834 A | 10/1996 | Hinchee et al. |
| 5,591,616 A | 1/1997 | Hiei et al. |
| 5,633,435 A | 5/1997 | Barry et al. |
| 5,635,055 A | 6/1997 | Sweet et al. |
| 5,780,708 A | 7/1998 | Lundquist et al. |
| 5,824,877 A | 10/1998 | Hinchee et al. |
| 5,837,848 A | 11/1998 | Ely et al. |
| 5,888,732 A | 3/1999 | Hartley et al. |
| 5,981,840 A | 11/1999 | Zhao et al. |
| 6,084,089 A | 7/2000 | Mine et al. |
| 6,118,047 A | 9/2000 | Anderson et al. |
| 6,140,078 A | 10/2000 | Sanders et al. |
| 6,160,208 A | 12/2000 | Lundquist et al. |
| 6,194,636 B1 | 2/2001 | McElroy et al. |
| 6,207,879 B1 | 3/2001 | McElroy et al. |
| 6,232,526 B1 | 5/2001 | McElroy et al. |
| 6,252,138 B1 | 6/2001 | Karimi et al. |
| 6,277,608 B1 | 8/2001 | Hartley et al. |
| 6,294,714 B1 | 9/2001 | Matsunaga et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,426,446 B1 | 7/2002 | McElroy et al. |
| 6,429,357 B1 | 8/2002 | McElroy et al. |
| 6,433,252 B1 | 8/2002 | Kriz et al. |
| 6,437,217 B1 | 8/2002 | McElroy et al. |
| 6,580,019 B1 | 6/2003 | McElroy et al. |
| 6,583,338 B2 | 6/2003 | McElroy et al. |
| 6,750,379 B2 | 6/2004 | McElroy et al. |
| 2002/0133852 A1 | 9/2002 | Hauge et al. |
| 2002/0192813 A1 | 12/2002 | Conner et al. |
| 2003/0005491 A1 | 1/2003 | Hauge et al. |
| 2003/0049612 A1 | 3/2003 | Echt et al. |
| 2003/0233670 A1 | 12/2003 | Edgerton et al. |
| 2004/0115642 A1 | 6/2004 | Fu |
| 2004/0123347 A1 | 6/2004 | Hinchey et al. |
| 2004/0126845 A1 | 7/2004 | Eenennaam et al. |
| 2004/0216189 A1 | 10/2004 | Houmard et al. |
| 2004/0244075 A1 | 12/2004 | Cai et al. |
| 2004/0268441 A1 * | 12/2004 | Vance et al. .................. 800/288 |
| 2005/0108791 A1 | 5/2005 | Edgerton |

FOREIGN PATENT DOCUMENTS

| | | |
|---|---|---|
| WO | WO 95/06128 A2 | 3/1995 |
| WO | WO 02/057471 A2 | 7/2002 |
| WO | WO 02/062129 A2 | 8/2002 |
| WO | WO 2004029257 A1 * | 4/2004 |

OTHER PUBLICATIONS

Van Houdt et al., Plant Physiol., 2003, vol. 131, pp. 245-253.*
Terada et al., Plant Cell Physiol., 2000, vol. 41, pp. 881-888.*
Shimada et al., Theor. Appl. Genet., 1993, vol. 86, pp. 665-672.*
Kyozuka et al., Mol. Gen. Genet., 1991, vol. 228, pp. 40-48.*
Waterhouse et al., PNAS, 1998, vol. 95, pp. 13959-13964.*
Bartel, Cell, Jan. 2004, vol. 116, pp. 281-297.*
Parizotto et al., Genes Devel., Sep. 2004, vol. 18, pp. 2237-2242.*
Chen et al. (2003) Plant J. 36: 731-740.*
An et al., "Functional Analysis of the 3' Control Region of the Potato Wound-Inducible Proteinase Inhibitor II Gene," *The Plant Cell*, 1:115-122 (1989).
Aslanidis et al., "Ligation-independent cloning of PCR products (LIC-PCR)," *Nucleic Acids Research*, 18(20):6069-6074 (1990).
Bayer et al., "Programmable ligand-controlled riboregulators of eukaryotic gene expression," *Nature Biotechnology*, 23(3):337-343 (2005).
Davidson et al., "Engineering regulatory RNAs," *TRENDS in Biotechnology*, 23(3):109-112(2005).
Isaacs et al., "Engineered riboregulators enable post-transcriptional control of gene expression," *Nature Biotechnology*, 22(7):841-847 (2004).
Lee et al., "Aptamer Database," *Nucleic Acids Research*, 32:D95-D100 (2004).

(Continued)

Primary Examiner — David H Kruse
Assistant Examiner — Steven Bernacki
(74) Attorney, Agent, or Firm — Amanda Carmany-Rampey; David R. Marsh; Arnold & Porter LLP

(57) ABSTRACT

This invention discloses methods for providing plants with selective expression of a target RNA and methods for evaluating an expression pattern of a target RNA in a plant. Also disclosed are transgenic plants having recombinant DNA for expressing a protein using a promoter functional in multiple tissues, and recombinant DNA for suppressing expression of the protein using a promoter functional in fewer than the multiple tissues.

14 Claims, 4 Drawing Sheets

(56) References Cited

OTHER PUBLICATIONS

Mandal et al., "Adenine riboswitches and gene activation by disruption of a transcription terminator," *Nature Struct. Mol. Biol.*, 11(1):29-35 (2004).

Mandal et al., "Gene Regulation by Riboswitches," *Nature Reviews | Molecular Cell Biology*, 5:451-463 (2004).

Matzke et al., "RNA-based silencing strategies in plants," *Curr. Opin. Gen. Dev.*, 11:221-227 (2001).

Meister et al., "Mechanisms of gene silencing by double-stranded RNA," *Nature*, 431:343-349 (2004).

Nimjee et al., "Aptamers: An Emerging Class of Therapeutics," *Annu. Rev. Med.*, 56:555-583 (2005).

Peng et al., "A Panoramic View of Yeast Noncoding RNA Processing," *Cell*, 113:919-933 (2003).

Rashtchian et al., "Uracil DNA Glycosylase-Mediated Cloning of Polymerase Chain Reaction-Amplified DNA: Application to Genomic and cDNA Cloning," *Analytical Biochemistry*, 206:91-97 (1992).

Rhoades et al., "Prediction of Plant MicroRNA Targets," *Cell*, 110:513-520 (2002).

Sudarsan et al., "Metabolite-binding RNA domains are present in the genes of eukaryotes," *RNA*, 9:644-647 (2003).

Szymanski et al., "Noncoding regulatory RNAs database," *Nucleic Acids Res.*, 31(1):429-431 (2003).

Tomari et al., "Perspective: machines for RNAi," *Genes Dev.*, 19:517-529 (2005).

Toulme et al., "Regulating eukaryotic gene expression with aptamers," *FEBS Letters*, 567:55-62 (2004).

Washietl et al., "Fast and reliable prediction of noncoding RNAs," *PNAS*, 102(7):2454-2459 (2005).

Winkler et al., "Thiamine derivatives bind messenger RNAs directly to regulate bacterial gene expression," *Nature*, 419:952-956 (2002).

\* cited by examiner

Wx transcript levels in 61 individual kernels from pMON81999 control constructs

Wx transcript levels in 10 individual kernels of ZM_M126880

SELECTIVE GENE EXPRESSION IN PLANTS

REFERENCE TO RELATED APPLICATIONS, AND INCORPORATION OF SEQUENCE LISTING

This application claims benefit of priority to U.S. Provisional Patent Application No. 60/715,632, filed on 9 Sep. 2005 and incorporated herein by reference. The sequence listing contained in the file named "38-15(53796)B.rpt", which is 2 kilobytes (measured in operating system MS-Windows), created on 8 Sep. 2006, and located in computer readable form on a compact disk (CD-R), is filed herewith and incorporated herein by reference. The sequence listing contained in the file "38-15(53796)A.rpt" (file size of 2 kilobytes), recorded on 8 Sep. 2005, and filed with U.S. Provisional Patent Application No. 60/715,632 on 9 Sep. 2005, is incorporated by reference herein.

FIELD OF THE INVENTION

The present invention discloses novel methods for providing plants with selective expression of a target RNA and methods for evaluating an expression pattern of a target RNA in a plant. Also disclosed are transgenic plants having recombinant DNA for expressing a protein using a promoter functional in multiple tissues, and recombinant DNA for suppressing expression of the protein using a promoter functional in fewer than the multiple tissues.

BACKGROUND OF THE INVENTION

Transgenic plant production generally uses a single promoter sequence and a single 3' untranslated region (UTR) to express a gene of interest in a transgenic plant. For example, a typical expression vector useful for expression of a gene of interest in maize includes a rice actin promoter and a 3' untranslated region of a potato protease inhibitor II gene (PinII 3' UTR, An et al. (1989) *Plant Cell*, 1: 115-122), flanking an open reading frame encoding the gene of interest. This method has been used to generate many transgenic events for different genes of interest, wherein all transgenic events share a common 3' UTR (see, for example, U.S. Patent Application Publications 2003/0233670 and 2005/0108791, which are incorporated by reference). In this example, each gene of interest is expected to be constitutively expressed under the control of the rice actin promoter. Where an altered or specific expression pattern of the gene of interest is desired, this is generally accomplished by placing the gene of interest under the control of a different promoter (e. g., a tissue specific or temporal specific promoter), and producing additional transgenic events. These additional differentially regulated events allow the researcher to, e. g., better understand gene function or to associate specific traits with the particular expression of the transgene. Unfortunately, the re-cloning and production of additional transgenic events is costly and time consuming.

The present invention provides novel methods for rapidly and conveniently assessing the effects of different promoters on the expression of a given gene of interest or target RNA. The methods are compatible with investigating transgenic events that already exist (for example, the large sets of transgenic plants provided in U.S. Patent Application Publications 2003/0233670 and 2005/0108791). An expression-specific promoter operably linked to DNA for suppressing expression of a target RNA or gene of interest is used to silence the expression of the target RNA in a plant. In one embodiment, the method is done through genetic crosses of a first parent plant (or set of first parent plants) containing a target RNA (e. g., one or more coding sequences that all use a common 3' UTR sequence that serves as the target RNA), with a second parent plant (or set of second parent plants), wherein each second parent plant has in its genome an expression-specific promoter operably linked to DNA for suppressing expression of the target RNA, and wherein the expression-specific promoter is different for each second parent plant. Preferably, such crosses produce hybrid progeny with selective expression of the target RNA relative to expression in the at least one first parent plant. The DNA for suppressing expression of the target RNA can be any DNA for gene suppression, including DNA that transcribes to single-stranded RNA or to double-stranded RNA or to both.

The invention provides rapid and convenient methods to alter, in a single generation, transgene expression patterns in a predetermined and rational manner. The methods are especially useful to allow the determination of tissues where expression of a gene of interest is desirable, e. g., in mode of action studies to determine where expression of a gene of interest is necessary or sufficient for activity. In a related utility, when creating transgenic plants for the purpose of screening genes for desired phenotypic effects, one may have only one or a few transgenic events displaying the desired phenotype; the invention provides methods by which one can confirm the function of a transgene by altering expression of the transgene in a given event. The method can also be used to optimize plant breeding strategies by allowing the alleviation of off types.

SUMMARY OF THE INVENTION

The present invention discloses methods for rapidly and conveniently assessing the effects of different promoters on the expression of a given gene of interest or target RNA One aspect of this invention provides a method of providing plants with selective expression of a target RNA, including: (a) providing at least one first parent plant producing target RNA; (b) providing a set of second parent plants, wherein each second parent plant has in its genome an expression-specific promoter operably linked to DNA for suppressing expression of said target RNA, and wherein the expression-specific promoter is different for each second parent plant; and (c) hybridizing the at least one first and each second parent plant, thereby producing hybrid progeny with selective expression of the target RNA relative to expression in the at least one first parent plant.

A second aspect of the invention provides a method of evaluating a non-constitutive, spatial, temporal, developmental, or inducible expression pattern of a target RNA in a plant, including: (a) performing crosses of at least one first plant with a set of second plants, wherein the at least one first plant expresses a target RNA, and each of the second plants has in its genome a silencing sequence including an expression-specific promoter operably linked to DNA for suppressing expression of the target RNA, wherein the expression-specific promoter is different for each of the second plants, and the crosses result in the formation of hybrid progeny; and (b) evaluating the hybrid progeny for a non-constitutive, spatial, temporal, developmental, or inducible expression pattern of the target RNA.

A third aspect of the invention provides a transgenic plant having recombinant DNA for expressing a protein using a promoter functional in multiple tissues and recombinant DNA for suppressing expression of said protein using a promoter functional in fewer than said multiple tissues. Other

DETAILED DESCRIPTION OF THE INVENTION

Figure 1:
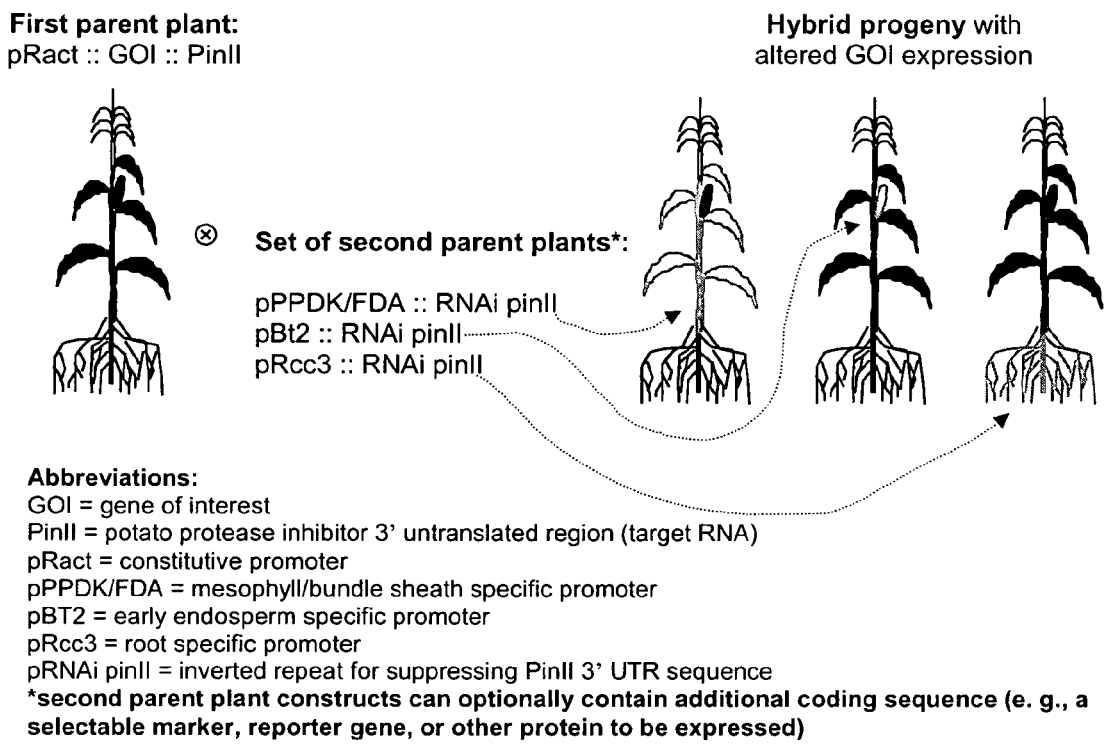
FIG. 1 is a schematic depiction of a method of providing plants with selective expression of a target RNA, as described in the specification and in Example 1.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Unless otherwise stated, nucleic acid sequences given in the text of this specification are in the 5' to 3' direction. Where a term is provided in the singular, the inventors also contemplate aspects of the invention described by the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries. The inventors do not intend to be limited to a mechanism or mode of action. Reference thereto is provided for illustrative purposes only.

A Method of Providing Plants With Selective Expression of a Target RNA

The present invention provides a method of providing plants with selective expression of a target RNA, including: (a) providing at least one first parent plant producing target RNA; (b) providing a set of second parent plants, wherein each second parent plant has in its genome an expression-specific promoter operably linked to DNA for suppressing expression of said target RNA, and wherein the expression-specific promoter is different for each second parent plant; and (c) hybridizing the at least one first and each second parent plant, thereby producing hybrid progeny with selective expression of the target RNA relative to expression in the at least one first parent plant.

Plants

Plants suitable as parent plants useful in the method can include can be any monocot or dicot plant of interest, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The at least one first parent plant and each of the set of second parent plants can be of the same or different line, variety, race, or species, as long as hybridizing them yields viable hybrid progeny. In many embodiments, the first parent and second parent plants are preferably of the same species but may be of the same or different line, variety, or race. In other embodiments, the first parent and second parent plants are preferably of the same line, variety, or race. In many embodiments, each second parent plant preferably differs from another only in terms of the expression-specific promoter that is operably linked to DNA for suppressing expression of said the RNA.

In some embodiments, the at least first parent plant is a single first parent plant (or multiple individual plants of identical "first parent plant" genetic constitution). In other embodiments, multiple first parent plants are used. In some embodiments, the set of second parent plants includes a single second parent plant (or multiple individual plants of identical "second parent plant" genetic constitution); in other cases, the set of second parent plants includes multiple, different second parent plants. In either case, each second parent plant has in its genome an expression-specific promoter operably linked to DNA for suppressing expression of the target RNA, and the expression-specific promoter is preferably different for each second parent plant. Crossing of the first and second parent plants may thus be carried out in a matrix fashion.

Target RNA

The at least one first parent plant is capable of producing a target RNA. The target RNA can be produced constitutively throughout the plant or only in specific cells, tissues, or organs, throughout the plant's growth cycle or only at particular times, under non-stress growing conditions or under periods of stress, or in any combination of these. Preferably, the spatial, temporal, and inducible or non-inducible expression of the target RNA is or can be characterized for the at least one first parent plant for comparison to expression in hybrid progeny.

The target RNA may be any RNA of interest for which selective expression is desired. The target RNA may be endogenous to the at least one first parent plant, for example, an RNA native to and found in a normal context or location in the first parent plant's genome. The target RNA may be exogenous to the at least one first parent plant, for example, an RNA introduced to the first parent plant by recombinant techniques such as plant transformation. Suitable exogenous target RNAs can include, for example, an RNA not native to the first parent plant, or a copy of an RNA native to the first parent plant but located in a non-natural context or location in the first parent plant's genome. The exogenous RNA may include a sequence identical to a sequence that is native to the first parent plant, or may include a sequence altered by addition and/or deletion of one or more nucleotides.

In some embodiments of the method of the invention, the target RNA includes coding RNA encoding a polypeptide sequence, which when translated results in the formation of a polypeptide or protein, for example, an enzyme or a structural protein. Coding RNA can also include RNA that encodes a signal peptide coding sequence or a transit peptide coding sequence, or other peptide sequence that may be cleaved from the maturing polypeptide or protein.

In other embodiments, the target RNA includes non-coding RNA. Non-coding RNA can include at least a part of at least one non-coding RNA element operably linked to RNA encoding a protein (for example, at least a part of a promoter, a promoter enhancer element, a 3' untranslated region, a 5' untranslated region, a polyadenylation sequence, and/or an intron). Non-coding RNA can include RNA sequence not directly involved with protein synthesis, for example, RNA encoding a gene suppression sequence, ribozyme, aptamer, riboswitch, microRNA, ribosomal RNA, transfer RNA, spliceosomal RNA, small nucleolar RNA, telomerase RNA, signal recognition particle RNA, the RNA components of RNase P and RNase MRP, chloroplastic rRNA, mitochondrial rRNA, internal ribosome entry site (IRES) RNA, or other RNAs that are not known or predicted to be translated into a polypeptide or protein (see, for example, Peng et al. (2003) *Cell,* 113:919-933, Szymanski et al. (2003) *Nucleic Acids Res.,* 31:429-431, Washietl et al. (2005) *Proc. Natl. Acad. Sci. USA,* 102:2454-2459, which are incorporated by reference in their entirety herein). A target RNA can also include a combination of coding and non-coding RNA.

Promoters

The method of the invention further provides a set of second parent plants, wherein each second parent plant has in its genome an expression-specific promoter operably linked to DNA for suppressing expression of the target RNA, and wherein the expression-specific promoter is different for each second parent plant. As used herein, "operably linked" refers to the expression-specific promoter's ability to regulate transcription of the DNA for suppressing expression of the target RNA. Suitable expression-specific promoters include a non-constitutive promoter, a spatially specific promoter, a temporally specific promoter, a developmentally specific promoter, and an inducible promoter. In other words, promoters useful in the invention include promoters that direct expression of the DNA for suppressing expression of the target RNA in a non-constitutive, spatially specific, temporally specific, developmentally specific, or inducible manner. By non-constitutive is meant a promoter that does not promote transcription of an operably linked sequence in all cells or all tissues at all times. Spatially specific promoters include organelle-, cell-, tissue-, or organ-specific promoters (e.g., a plastid-specific, a root-specific, or a seed-specific promoter for suppressing expression of the target RNA in plastids, roots, or seeds, respectively). Specific promoters of particular interest include, but are not limited to promoters that are specific to root, combined green tissues, mesophyll, bundle sheath, meristem, vascular tissue, early endosperm, mid-to-late endosperm, pollen, maize silk, and embryo.

Temporally specific promoters include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e.g., water deficit or drought, heat, cold, nutrient or salt levels, high or low light levels, or pest or pathogen infection). Expression-specific promoters further include promoters that are generally constitutively expressed but at differing degrees or "strengths" of expression relative to each other, including promoters commonly regarded as "strong promoters" or as "weak promoters".

Many expression-specific promoters functional in plants and useful in the method of the invention are known in the art. For example, U.S. Pat. Nos. 5,837,848; 6,437,217 and 6,426,446 disclose root specific promoters; U.S. Pat. No. 6,433,252 discloses a maize L3 oleosin promoter; U.S. Patent Application Publication 2004/0216189 discloses a promoter for a plant nuclear gene encoding a plastid-localized aldolase; U.S. Pat. No. 6,084,089 discloses cold-inducible promoters; U.S. Pat. No. 6,140,078 discloses salt inducible promoters; U.S. Pat. No. 6,294,714 discloses light-inducible promoters; U.S. Pat. No. 6,252,138 discloses pathogen-inducible promoters; and U.S. Patent Application Publication 2004/0123347 A1 discloses water deficit-inducible promoters. All of the above-described patents disclosing promoters and their use, especially in recombinant DNA constructs functional in plants are incorporated herein by reference.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.,* 22:841-847, Bayer and Smolke (2005) *Nature Biotechnol.,* 23:337-343, Mandal and Breaker (2004) *Nature Rev. Mol. Cell Biol.,* 5:451-463, Davidson and Ellington (2005) *Trends Biotechnol.,* 23:109-112, Winkler et al. (2002) *Nature,* 419: 952-956, Sudarsan et al. (2003) *RNA,* 9:644-647, and Mandal and Breaker (2004) *Nature Struct. Mol. Biol.,* 11:29-35, all of which are incorporated by reference herein. Such "riboregulators" could be selected or designed for specific spatial or temporal specificity, for example, to regulate translation of the exogenous gene only in the presence (or absence) of a given concentration of the appropriate ligand.

DNA for Suppressing

The DNA for suppressing can include DNA that is transcribed to single-stranded RNA or to double-stranded RNA or to both. Such suppression can involve any suitable mechanism for suppressing expression of a target RNA. These mechanisms include post-transcriptional gene suppression (suppressing production of protein translated from an RNA transcript) and transcriptional suppression (suppressing formation of an RNA transcript).

Suitable DNA for suppressing useful in the methods of the invention includes at least one suppression element (and, in some embodiments, multiple suppression elements) selected from the group consisting of:

(a) DNA that includes at least one anti-sense DNA segment that is anti-sense to at least one segment of the target RNA;

(b) DNA that includes multiple copies of at least one anti-sense DNA segment that is anti-sense to at least one segment of the target RNA;

(c) DNA that includes at least one sense DNA segment that is at least one segment of the target RNA;

(d) DNA that includes multiple copies of at least one sense DNA segment that is at least one segment of the target RNA;

(e) DNA that transcribes to RNA for suppressing the target RNA by forming double-stranded RNA and includes at least one anti-sense DNA segment that is anti-sense to at least one segment of the target RNA and at least one sense DNA segment that is at least one segment of the target RNA;

(f) DNA that transcribes to RNA for suppressing the target RNA by forming a single double-stranded RNA and includes multiple serial anti-sense DNA segments that are anti-sense to at least one segment of the target RNA and multiple serial sense DNA segments that are at least one segment of the target RNA;

(g) DNA that transcribes to RNA for suppressing the target RNA by forming multiple double strands of RNA and includes multiple anti-sense DNA segments that are anti-sense to at least one segment of the target RNA and multiple sense DNA segments that are at least one segment of the target RNA, and wherein the multiple anti-sense DNA segments and the multiple sense DNA segments are arranged in a series of inverted repeats;

(h) DNA that includes nucleotides derived from a miRNA; and (i) DNA that includes nucleotides of a siRNA.

Thus, in some embodiments, the DNA for suppressing includes DNA that transcribed to single-stranded RNA (ssRNA), for example, ssRNA including sense or anti-sense sequence for suppressing expression of the target RNA. For example, the DNA for suppressing can transcribe to ssRNA including tandem repeats of a sense or anti-sense sequence corresponding to (and capable of suppressing expression of) the target RNA. In other embodiments of the invention, the DNA for suppressing preferably includes DNA that is transcribed to double-stranded RNA capable of suppressing expression of the target RNA. See, for example, Matzke et al (2001) *Curr. Opin. Gen. Dev.*, 11:221-227 (2001), Meister & Tuschl (2004) *Nature*, 431:343-349, and Tomari and Zamore 2005) *Genes Dev.*, 19:517-529, for reviews of gene suppression. Post-transcriptional gene suppression is believed to be mediated by double-stranded RNA (dsRNA) having homology to a gene targeted for suppression. These dsRNAs include short interfering RNAs (siRNAs), which are believed to generally guide mRNA degradation, and microRNAs (miRNAs), which are believed to generally mediate translational suppression but which may also guide mRNA degradation. Gene suppression by RNA transcribed from an exogenous DNA construct including an inverted repeat of at least part of a transcription unit is a common feature of gene suppression methods known variously as anti-sense suppression, co-suppression, and RNA interference. Transcriptional suppression can also be mediated, for example, by a transcribed double-stranded RNA having homology to, for example, promoter DNA sequence, to effect what is called trans-suppression (e. g., promoter trans-suppression). In other embodiments of the invention, gene suppression can also be obtained by means of a DNA or RNA aptamer or by a chimeric molecule including an aptamer, as is known in the art (see, for example, Toulme et al. (2004) *FEBS Lett.*, 567: 55-62, Lee, et al. (2004) *Nucleic Acids Res.*, 32:95-100, Nimjee et al. (2005) *Ann. Rev. Med.*, 56:555-583, and Bayer and Smolke (2005), *Nature Biotechnol.*, 23:337-343, which are incorporated herein by reference in their entirety).

The DNA for suppressing can include sense, anti-sense, or both sense and anti-sense sequence corresponding to the target RNA. Where the target RNA includes coding RNA, the DNA for suppressing can include sense, anti-sense, or both sense and anti-sense sequence for the coding region included in the target RNA. Where the target RNA includes non-coding RNA, the DNA for suppressing can include sense, anti-sense, or both sense and anti-sense sequence for the non-coding region included in the target RNA. Where a target RNA includes a combination of coding and non-coding RNA, the DNA for suppressing can include sense, anti-sense, or both sense and anti-sense sequence for the coding region, the non-coding region, or both the coding and non-coding regions included in the target RNA. The DNA for suppressing can include additional sequence, such as spacer sequence or linker sequence.

In one preferred, but non-limiting, embodiment, the DNA for suppressing expression of the target RNA includes a DNA encoding one or more microRNAs that target the 3' UTR common to a set of transgenic events (i. e., in the first parent plants). Alternatively, the DNA for suppressing expression can be designed to transcribe to RNA that lacks functional nuclear export signals and thus remains in the nucleus where it suppresses nuclear targets (e. g., nuclear mRNAs). RNA that lacks functional nuclear export signals includes RNA where at least one of a functional polyadenylation signal and a functional polyadenylation site is absent, or RNA where a 3' untranslated region is absent, or RNA that includes a self-splicing ribozyme located adjacent to and 3' to the suppression element; or RNA wherein the suppression element is embedded in an intron. These embodiments may be especially useful where non-systemic spreading of silencing is not desired.

Transgenic Plants

The first parent plant can be a transgenic plant or can be a naturally occurring or "wild type" plant. In general, the set of second parent plants are transgenic plants. Transgenic first parent or second parent plants can be provided by means of transgenic plant techniques known to those of ordinary skill in the art in light of this disclosure. Introduction into the genome of each second parent plant of the expression-specific promoter operably linked to DNA for suppressing expression of the target RNA can make use of a recombinant "cassette" typically provided using one or more transformation vectors. General methods for making and using DNA constructs and vectors that can be employed in conjunction with plant transformation techniques useful in the method are well known in the art. See, for example, handbooks and laboratory manuals including Sambrook and Russell, "Molecular Cloning: A Laboratory Manual" (third edition), Cold Spring Harbor Laboratory Press, NY, 2001, which is incorporated herein by reference. Many approaches or methods have been developed and used for gene cloning. Examples of these are cloning by restriction enzyme digestion and ligation of compatible ends, T-A cloning directly from PCR product, TOPO-attached unidirectional cloning, and recombination-based cloning. Examples of useful technology for building DNA constructs and vectors for plant transformation are disclosed in U.S. Patent Application Publication Numbers 2002/0192813 A1 and 2004/0115642 A1, which are incorporated by reference in their entirety herein. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051, all of which are incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

It is specifically contemplated by the inventors that one can use techniques for the site-specific integration or excision of transformation constructs for providing parent plants useful in the method of the invention. An advantage of site-specific integration or excision is that it can be used to overcome problems associated with conventional transformation techniques, in which transformation constructs typically randomly integrate into a host genome and multiple copies of a construct may integrate. This random insertion of introduced DNA into the genome of host cells can be detrimental to the cell if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration can be achieved in plants by means of homologous recombination. DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events).

A number of different site specific recombinase systems could be employed to provide parent plants useful in the method of the invention, including, but not limited to, the Cre/lox system of bacteriophage P1, the FLP/FRT system of yeast, the Gin recombinase of phage Mu, the Pin recombinase of *E. Coli*, and the R/RS system of the pSR1 plasmid. The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors. The FLP/FRT and Cre/lox recombinase systems have been demonstrated to function efficiently in plant cells. A more thorough discussion of site-specific integration or excision of transgenes, particularly in regard to their use in transgenic plants, can be found in, for example, U.S. Pat. Nos. 4,959,317 and 5,527,695, both of which are incorporated herein by reference in their entirety.

During the transformation process it is often necessary to include ancillary sequences, such as selectable marker or reporter genes, e. g., for tracking the presence or absence of a desired trait gene transformed into the plant on the DNA construct. Such ancillary sequences often do not contribute to the desired trait or characteristic conferred by the phenotypic trait gene. Homologous recombination is a method by which introduced sequences can be selectively deleted in transgenic plants.

Homologous recombination can result in genetic rearrangements of transgenes in plants. Deletion of sequences by homologous recombination relies upon directly repeated DNA sequences positioned about the region to be excised in which the repeated DNA sequences direct excision utilizing native cellular recombination mechanisms. For example, a first fertile transgenic plant can be crossed to produce either hybrid or inbred progeny plants, and from those progeny plants, one or more second fertile transgenic plants can be selected which contain a second DNA sequence that has been altered by recombination, preferably resulting in the deletion of the ancillary sequence. The first fertile plant can be either hemizygous or homozygous for the DNA sequence containing the directly repeated DNA which will drive the recombination event.

The directly repeated sequences are located 5' and 3' to the target sequence in the transgene. As a result of the recombination event, the transgene target sequence can be deleted, amplified or otherwise modified within the plant genome. In a particularly preferred embodiment, a deletion of the target sequence flanked by the directly repeated sequence will result. See, for example, U.S. Pat. Nos. 6,580,019 and 6,750,379, both of which are incorporated herein by reference in their entirety, for additional discussion of the deletion of sequences located within a transgenic insert.

Suitable transformation methods to provide parent plants useful in the method of the invention include virtually any method in the art by which DNA can be introduced into a plant cell, such as by direct delivery of DNA such as by PEG-mediated transformation of protoplasts, by electroporation, by agitation with silicon carbide fibers, by *Agrobacterium*-mediated transformation, and by acceleration of DNA coated particles, etc. Preferred methods of plant transformation include, but are not limited to, microprojectile bombardment as illustrated, for example, in U.S. Pat. Nos. 5,015,580, 5,550,318, 5,538,880, 6,160,208, 6,399,861, and 6,403,865 and *Agrobacterium*-mediated transformation as illustrated, for example, in U.S. Pat. Nos. 5,635,055, 5,824,877, 5,591,616, 5,981,840, and 6,384,301, all of which are incorporated herein by reference. Through the application of techniques such as these, cells of virtually any plant species of interest can be stably transformed, and these cells developed into transgenic parent plants useful in the method of the invention. Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. Nos. 5,591,616 and 5,981,840 (maize); U.S. Pat. No. 5,463,174 (brassicas), and in U.S. Patent Application Publication 2004/0244075 (maize), all of which are incorporated by reference. Single or multiple recombinant constructs can be used for transforming plants useful in the method; for example, constructs for coordinated decrease and increase of gene expression are disclosed in U.S. Patent Application Publication Number 2004/

0126845 to Van Eenennaam et al., which is incorporated by reference herein. Seeds of plants (including first or second parent plants and their hybrid progeny) can be harvested from fertile transgenic plants and be used to grow progeny generations, including hybrid or inbred plant lines.

Transformation procedures to provide first or second parent plants of the invention are generally preferably practiced in tissue culture on media and in a controlled environment. "Media" refers to the numerous nutrient mixtures that are used to grow cells in vitro, that is, outside of the intact living organism. A preferred medium is a suspension of various categories of ingredients (salts, amino acids, growth regulators, sugars, buffers) that are required for growth of a cell type of interest. However, it is well known in the art that each specific cell type requires a specific range of ingredient proportions for growth, and an even more specific range of formulas for optimum growth. Rate of cell growth also will vary among cultures initiated with the array of media that permit growth of that cell type.

Recipient cell targets for transformation include, but are not limited to, meristem cells, callus, immature embryos (intact or partial), and gametic cells such as microspores, pollen, sperm, and egg cells. It is contemplated that any cell from which a fertile plant can be regenerated is useful as a recipient cell. Callus can be initiated from tissue sources including, but not limited to, immature embryos (intact or partial), seedling apical meristems, microspores, and the like. Those cells which are capable of proliferating as callus also are suitable recipient cells for genetic transformation. The present invention provides techniques for transforming immature embryos and subsequent regeneration of fertile transgenic plants. Practical transformation methods and materials for making transgenic plants useful in methods of the invention, e. g., various media and recipient target cells, transformation of immature embryos and subsequent regeneration of fertile transgenic plants are disclosed, for example, in U.S. Pat. No. 6,194,636 and U.S. Patent Application Publication Number 2004/0216189, which are incorporated by reference in their entirety herein.

After effecting delivery of exogenous DNA to recipient cells, the next steps generally concern identifying the transformed cells for further culturing and plant regeneration. In order to improve the ability to identify transformants, one can employ a selectable or screenable marker gene as, or in addition to, the expressible gene of interest (such as a target RNA). In this case, one could then assay the potentially transformed cell population by exposing the cells to a selective agent or agents, or one could screen the cells for the desired marker gene trait.

It is believed that DNA is introduced into only a small percentage of target cells in any one experiment. In order to provide an efficient system for identification of those cells receiving DNA and integrating it into their genomes, one can employ a means for selecting those cells that are stably transformed. One exemplary embodiment of such a method is to introduce into the host cell a marker gene which confers resistance to some normally inhibitory agent, such as an antibiotic or herbicide. Non-limiting examples of marker genes which can be used include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS or CP4). Use of such selectable markers is illustrated in, for example, U.S. Pat. Nos. 5,550,318, 5,633,435, 5,780,708, and 6,118,047, all of which are incorporated herein by reference. Screenable markers which provide an ability to visually identify transformants can also be employed, e. g., a gene expressing a colored or fluorescent protein such as a luciferase or green fluorescent protein (GFP), or a gene expressing a beta-glucuronidase or uidA gene (GUS) for which various chromogenic substrates are known. Cells that survive the exposure to the selective agent, or cells that have been scored positive in a screening assay, can be cultured in media that supports regeneration of transgenic plants useful in the method of the invention.

To confirm the presence of an exogenous DNA or RNA in regenerated plants (or in their hybrid offspring), a variety of assays can be performed, e. g., to detect the presence of an exogenous DNA or RNA directly or to detect the presence or absence of a protein encoded by the exogenous DNA. Such assays include, for example, molecular assays for detecting a nucleic acid, e. g., by Southern or Northern blotting or PCR or other nucleic acid amplification methods; biochemical assays such as detecting the presence of a protein product, e. g., by immunological means (ELISAs and Western blots) or by enzymatic function; plant part assays such as leaf or root assays; and in some cases phenotypic analysis of a whole regenerated plant, including phenotypic analysis of a whole, field-grown plant. Additional assays useful for determining the efficiency of transgene expression and promoter function also include, without limitation, fluorescent in situ hybridization (FISH), direct DNA sequencing, pulsed field gel electrophoresis (PFGE) analysis, single-stranded conformation analysis (SSCA), RNase protection assay, allele-specific oligonucleotide (ASO), dot blot analysis, denaturing gradient gel electrophoresis, RT-PCR, quantitative RT-PCR, RFLP, and PCR-SSCP. Such assays are well known to those of ordinary skill in the art.

Hybridizing or Crossing

The at least one first parent plant and set of second parent plants are hybridized, or crossed, thereby producing hybrid progeny with selective expression of the target RNA relative to expression in the at least one first parent plant. Hybrid progeny can include hybrid progeny seed, hybrid progeny plants of any developmental stage grown from such seed, or both. It is envisioned that progeny from a hybridization between the at least first parent and a given second parent plant with a specific expression-specific promoter will display expression of the target RNA in a selective manner (relative to the expression in the first parent plant), depending on the specificity of the promoter of the second parent plant used in the hybridization. Hybridization of the at least one first parent plant with the set of second parent plants can occur in one period (typically days or weeks) or over multiple periods or seasons or even years. In one embodiment, hybridization is performed so that expression of the target RNA can be compared between hybrid progeny and the first parent plant in one set of comparisons carried out substantially simultaneously (generally in a single experiment). For example, hybrid progeny seed can be prepared from hybridization of the first parent plant and a set of second parent plants, and expression of the target RNA is compared between the hybrid seed and seed from the first parent plant, or hybrid seed and seed from the first parent plant are germinated and expression of the target RNA compared between the resulting plants. In another embodiment, hybridization and/or assaying expression of the target RNA can be carried out over different seasons or even years.

Hybridization (or crossing) can include, for example, pollination of flowers of one parent plant with pollen from another parent plant. Either the at least one first parent plant or the set of second parent plants can serve as pollinators.

Hybrid progeny seeds from the parent plant bearing the fertilized flower can be harvested and optionally grown into hybrid progeny plants.

Hybrid progeny can be further developed into derivative plants by additional crossing steps. It is often desirable to introgress a DNA construct into elite varieties, e. g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i. e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different derivative hybrids with different combinations of DNA constructs. In this way, plants can be produced which have the desirable agronomic properties frequently associated with "hybrid vigor", as well as the desirable characteristics imparted by one or more DNA constructs.

Genetic markers can be used to assist in the introgression of one or more DNA constructs from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491, each of which is incorporated herein by reference in their entirety.

The ultimate goal in plant transformation is to produce plants which are useful to man. In this respect, hybrid plants created in accordance with the method of the invention can be used for virtually any purpose deemed of value to the grower or to the consumer. For example, one may wish to harvest seed for planting purposes, or products can be made from the seed itself such as oil, starch, animal or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471, each of which is incorporated herein by reference in its entirety.

Selective Expression

The method of the invention preferably results in hybrid progeny (seeds or plants grown from such seeds, or both) with selective expression of the target RNA relative to expression in the at least one first parent plant. Expression of the target RNA (or of a polypeptide or protein encoded by the target RNA) can be evaluated using any suitable technique, including molecular or biochemical assays well known in the art (such as, but not limited to, Southern or Northern blots, RT-PCR, in situ hybridization, Western blots, ELISAs, enzyme assays, in situ immunological or enzymatic labeling); see also, for example, techniques for confirming thee presence of an exogenous DNA or RNA discussed above under the heading "Transgenic Plants", and various assays for nucleic acid or protein expression described in Sambrook and Russell, "Molecular Cloning: A Laboratory Manual" (third edition), Cold Spring Harbor Laboratory Press, N.Y., 2001, which is incorporated herein by reference. Expression of the target RNA can be evaluated by microscopic or gross morphological, physiological, or phenotypic observations in the laboratory, greenhouse, or field, including cell or tissue assays (such as leaf or root assays) or observations of intact greenhouse- or field-grown plants. Where the plant is a crop plant, of particular interest is selective expression of the target RNA that results in changes in agronomic traits of interest, such as, but not limited to, resistance or tolerance to herbicides, pesticides, diseases, pests, or pathogens, resistance or tolerance to environmental stresses (for example, salt stress, water-deficit stress, nutrient stress, or temperature stress), reproductive success, yield, or nutritional or processing quality of the harvested crop.

Generally, expression of the target RNA is compared between hybrid progeny and the at least one first parent plant; such comparison can occur substantially simultaneously (e. g., on the same day or within a period of a few days) or at different times (e. g., comparison can be made between plants grown at different seasons or even over different years).

In some embodiments, expression of the target RNA can be selective, or different relative to expression in the at least one first parent plant, in a spatial, temporal, or inducible manner. For example, the expression of the target RNA can occur or can be suppressed whole or partially in different organelles, cells, tissues, or organs in hybrid progeny, so as to produce a pattern of expression different from that observed in the first parent plant. Expression of the target RNA can occur in hybrid progeny at developmental stages in the plants' growth cycle, or during times of day or night, or at seasons in a year different from that observed in the first parent plant. Expression of the target RNA can be induced by chemicals or by environmental conditions (such as, but not limited to, biotic or abiotic stress) in hybrid progeny differently that in the first parent plant. In some embodiments, the expression of the target RNA in hybrid progeny can be selective, or different from that in the at least one first parent plant, in a manner of degree. For example, the expression of the target RNA can be at a high level in the first parent plant, and at a relatively moderate or low level in hybrid progeny.

Method of Evaluating Expression Patterns of a Target RNA

The present invention also provides a method of evaluating a non-constitutive, spatial, temporal, developmental, or inducible expression pattern of a target RNA in a plant, including: (a) performing crosses of at least one first plant with a set of second plants, wherein the at least one first plant expresses a target RNA, and each of the second plants has in its genome a silencing sequence including an expression-specific promoter operably linked to DNA for suppressing expression of the target RNA, wherein the expression-specific promoter is different for each of the second plants, and the crosses result in the formation of hybrid progeny; and (b) evaluating the hybrid progeny for a non-constitutive, spatial, temporal, developmental, or inducible expression pattern of the target RNA.

The method can be used to evaluate expression patterns of a target RNA in any plant of interest, as described above under the heading "Plants", including any monocot or dicot plant of interest, such as crop plants, wood- or pulp-producing trees, vegetable plants, fruit plants, and ornamental plants. Preferred monocot plants include, but are not limited to, wheat, oat, barley, maize, rye, triticale, rice, ornamental and forage grasses, sorghum, millet, and sugarcane, more preferably maize, wheat, and rice. Preferred dicot plants include, but are not limited to, canola, cotton, potato, quinoa, amaranth, buckwheat, safflower, soybean, sugarbeet, and sunflower, more preferably soybean and cotton.

The at least one first plant expresses a target RNA, which can be coding RNA, non-coding RNA, or both coding and non-coding RNA, as described above under the heading "Target RNA". The target RNA can be endogenous or exogenous to the at least one first plant. Preferably, the non-constitutive, spatial, temporal, developmental, or inducible expression pattern of the target RNA is or can be characterized for the at least one first plant for comparison to expression in hybrid progeny.

Each of the second plants has in its genome a silencing sequence including an expression-specific promoter operably linked to DNA for suppressing expression of the target RNA, wherein the expression-specific promoter is different for each of the second plants. Suitable expression-specific promoters include promoters having non-constitutive, spatial, temporal, developmental, or inducible promoter activity, or promoters that are generally constitutively expressed but at differing degrees or "strengths" of expression, as described above under the heading "Promoters". The DNA for suppressing expression of the target RNA is described above under the heading "DNA for Suppressing. In many embodiments, the DNA for suppressing preferably includes DNA that is transcribed to double-stranded RNA capable of suppressing expression of the target RNA, and such suppression can involve any suitable double-stranded RNA-mediated silencing mechanism for suppressing expression of a target RNA (e.g., post-transcriptional gene suppression and transcriptional suppression or suppression by an aptamer-mediated mechanism). The DNA for suppressing can include sense, anti-sense, or both sense and anti-sense sequence corresponding to the target RNA, or can be transcribed to a suppressing RNA that suppresses expression of the target RNA.

The at least one first plant and each of the set of second plants can be of the same or different line, variety, race, or species, as long as crossing them yields viable hybrid progeny. In many embodiments, the first and second plants are preferably of the same species but can be of the same or different line, variety, or race. In other embodiments, the first and second plants are preferably of the same line, variety, or race. Preferably, each second plant differs from another only in terms of the expression-specific promoter in its genome. The first plant can be a transgenic plant or can be a naturally occurring or "wild type" plant. In general, the set of second plants are transgenic plants. Transgenic first or second plants can be provided by means of transgenic plant techniques as described above under the heading "Transgenic Plants".

The at least one first plant is crossed with each of a set of second plants to result in the formation of hybrid progeny. Crossing is performed as described above under the heading "Hybridization or Crossing". Hybrid progeny can include hybrid progeny seed, hybrid progeny plants of any developmental stage grown from such seed, or both. Hybridization of the at least one first plant with the set of second plants can occur in one period (typically days or weeks) or over multiple periods or seasons or even years. Hybridization (or crossing) can include, for example, pollination of flowers of one plant with pollen from another plant. Either the at least one first plant or the set of second plants can serve as pollinators. Hybrid progeny seeds from the plant bearing the fertilized flower can be harvested and optionally grown into hybrid progeny plants. Hybrid progeny can be further developed into derivative plants by additional crossing steps.

The hybrid progeny are evaluated for spatial, temporal, or inducible expression patterns of the target RNA. It is envisioned that expression of the target RNA will be selective, or different in the hybrid progeny than in the first plant from which the hybrid progeny are derived. Evaluation of target RNA expression can make use of any technique as described above under the heading "Selective Expression", including molecular or biochemical techniques, or microscopic or gross morphological, physiological, or phenotypic observations in the laboratory, greenhouse, or field. Comparison of target RNA expression can be made substantially simultaneously or at different times for the hybrid progeny and first plant from which the hybrid progeny are derived. Where the plant is a crop plant, of particular interest is selective expression of the target RNA that can result in changes in agronomic traits of interest.

Transgenic Plant Having Selective Expression

The present invention further provides a transgenic plant having recombinant DNA for expressing a protein using a promoter functional in multiple tissues and recombinant DNA for suppressing expression of said protein using a promoter functional in fewer than said multiple tissues. The transgenic plant preferably has selective expression of the protein, that is, expression of the protein that is different from that in at least one progenitor plant (such as a parent or other ancestral plant) from which the transgenic plant is derived.

The transgenic plant of the invention can be provided by hybridization or crossing of two plants, preferably by use of the methods of the invention described herein. In one preferred embodiment, the transgenic plant is a hybrid plant obtained by hybridization or crossing of one plant that has recombinant DNA for expressing a protein using a promoter functional in multiple tissues and another plant that has recombinant DNA for suppressing expression of said protein using a promoter functional in fewer than said multiple tissues. In another preferred embodiment, the transgenic plant is a derivative plant derived from such a hybrid plant, for example, by back-crossing, out-crossing, or self-crossing of such a hybrid plant. In more preferred embodiments and where the transgenic plant is a crop plant, the selective expression of the protein in the transgenic plant results in desirable or enhanced agronomic traits (for example, improved resistance or tolerance to herbicides, pesticides, diseases, pests, or pathogens, improved resistance or tolerance to environmental stresses, improved reproductive success, and improved yield or quality of the harvested crop) in the transgenic plant in comparison to at least one progenitor plant from which the transgenic plant is derived.

EXAMPLES

Example 1

This example illustrates a non-limiting example of a method of providing plants with selective expression of a target RNA. More specifically, in this example an expression-specific promoter operably linked to DNA for suppressing expression of a target RNA or gene of interest is used to silence the expression of the target RNA in a plant. A first parent plant (or set of first parent plants) containing a target RNA is crossed with a second parent plant (or set of second parent plants), wherein each second parent plant has in its genome an expression-specific promoter operably linked to DNA for suppressing expression of the target RNA, and wherein the expression-specific promoter is different for each second parent plant.

In one non-limiting embodiment, the first parent plants are transgenic for a construct including a constitutive promoter (e. g., a CaMV 35S promoter or a rice actin promoter) that directs expression of one or more coding sequences, wherein the constructs share a common target RNA (in this example, the PinII 3' UTR, see An et al. (1989) *Plant Cell*, 1:115-122, which is incorporated by reference herein). The coding sequence can encode any gene of interest (such as, but not limited to, green fluorescent protein (GFP), beta-glucoronidase (gus), a *Bacillus thurigensis* (Bt) insecticidal protein, or an enzyme involved in amino acid or fatty acid synthesis or catabolism, or a sequence for silencing a target gene), and all of these coding sequences can use the same 3' UTR which is transcribed to a common target RNA. U.S. Patent Application Publications 2003/0233670 and 2005/0108791, which are incorporated by reference herein, provide detailed procedures to make sets of transgenic plants, any or all of which are useful as first parent plants of the present invention, and which are made using a cloning cassette (into which can be inserted a gene of interest) flanked 5' by a rice actin 1 promoter, exon, and intron, and flanked 3' by the pinII 3' UTR gene.

These first parent plants are crossed in a matrix fashion to a set of second parent plants that are transgenic for a construct including an expression-specific promoter operably linked to DNA for suppressing expression of the target RNA (i. e., the PinII 3' UTR). The DNA for suppressing expression is an inverted repeat that targets the PinII 3' UTR, but can be any other DNA for suppressing (such as, but not limited to, tandem repeats or anti-sense) (see FIG. 1). The constructs in the second parent plants can optionally also include a coding sequence (e. g., encoding a selectable marker, or a reporter gene, or another protein to be expressed) driven by the expression-specific promoter. The resulting hybrid seed (or progeny plants grown from the hybrid seed) are evaluated for expression patterns of the coding sequence(s) (see FIG. 1).

In one non-limiting, specific case, the coding sequence in the first parent plant is gfp, which encodes green fluorescent protein (GFP), with the PinII 3' UTR and under the control of a CaMV35S promoter. A convenient alternative to GFP is uidA, which encodes beta-glucuronidase or GUS. The first parent plant is crossed with a set of second parent plants, wherein each second parent plant is transgenic for a tissue-specific promoter operably linked to DNA for suppressing expression of said target RNA, wherein the DNA for suppressing includes a microRNA (miRNA) designed to target the PinII 3' UTR sequence, and wherein the tissue-specific promoter is different for each second parent plant. The miRNA is designed using suitable methods, such as, but not limited to, bioinformatics prediction modelling using known primary and secondary miRNA sequence requirements (e. g., an imperfectly hybridizing stem structure and a non-self-hybridizing open loop, along with partial complementarity to at least a segment of the target, i. e., the PinII 3' UTR region). See, for example, Rhodes et al. (2002) *Cell*, 110:513-520, who describe examples of miRNA design.

Hybrid seed from the crosses are collected and germinated into progeny plants. The presence (or absence) of green fluorescent protein in the hybrid seed or progeny plants grown from the hybrid seed is visually evaluated for tissue-specific expression patterns. For example, progeny plants grown from hybrid seed resulting from a cross of the first parent plant with a second parent plant, wherein the tissue-specific promoter is a root-specific promoter, would show suppression of GFP fluorescence in the root (the suppression being relative to GFP fluorescence in the first parent plant). Thus, by using a set of second parent plants, each having in its genome a different specific promoter operably linked to DNA for suppressing a target RNA, a researcher is able to conveniently suppress the target RNA (e. g., the PinII 3' UTR, or a coding sequence operably linked to the PinII 3' UTR) simply by performing genetic crosses. The method of the invention makes it possible to take even a large set of first parent plants (such as the transgenic plants described in U.S. Patent Application Publications 2003/0233670 and 2005/0108791, where each expresses a different gene of interest but contains a common target RNA), and to obtain, in a single generation, hybrid progeny with selective expression of the target RNA (and thus of the genes of interest). Where a gene of interest is a gene silencing sequence, the hybrid progeny show selective expression of the gene silencing sequence (i. e., selective gene silencing).

In some embodiments of this approach, a selectable marker (or a reporter gene) is linked to the miRNA (or other DNA for suppressing). This permits one to select for (or to monitor) subsequent progeny of the original genetic cross. For example, if the original event (e. g., the target RNA) was linked to the NptII marker (encoding kanamycin resistance) and the DNA for suppressing (e. g., an miRNA) was linked to the CP4 gene (encoding glyphosate resistance), then the F2 and subsequent generations of progeny plants can be selected (or monitored) for either or both kanamycin resistance and glyphosate resistance, which thus indicate the genetic makeup of the progeny. In other embodiments of this approach, the DNA for suppressing the target RNA (e. g., a miRNA) is under the control of a chemically inducible (or chemically suppressible) promoter or other regulatory element (e. g., a riboswitch). This permits suppression (or allowed expression) of the target RNA under chemically induced conditions, which can be induced as necessary.

Example 2

This example illustrates a non-limiting example of a first parent plants that can be used in the method of providing plants with selective expression of a target RNA. More specifically, this example illustrates generation and use of a novel Wx-suppression transgene that is inherited in a dominant manner and provides a visually identifiable, dominantly heritable non-starchy phenotype, useful for efficient backcrossing in maize. Such transgenic plants can serve as first parent plants of the method, and crossed with a set of second parent plants to obtain progeny plants wherein the non-starchy phenotype can be selectively expressed (e. g., by means of specific promoters).

The dominant Waxy gene in maize encodes an enzyme for starch synthesis and homozygous (Wx/Wx) and heterozygous (Wx/wx) plants display a "starchy" phenotype with sufficient amylose (straight-chain) starch present in the endosperm or mature pollen to stain dark purple with iodine/potassium iodide ($I_2$/KI) solution (see p. 115, Sheridan (editor), "Maize for Biological Research", University Press, Grand Forks, N. Dak., 1982). The "waxy" (non-starchy) mutant phenotype, with decreased amylose and increased amylopectin (branched starch), is typically seen in plants homozygous for the naturally occurring, recessive allele (wx/wx). The waxy phenotype is useful as a visual marker of inheritance in maize breeding.

Conventional breeding practice for producing waxy (wx/wx) maize hybrids uses "backcross breeding". A line carrying a waxy recessive mutation is introduced into elite inbred lines and this mutation is then fixed in the elite background by backcrossing to the elite line. Backcross breeding typically involves at least six generations of backcrossing, with selection of a heterozygous waxy line (which is phenotypically normal, i. e., starchy) in each generation. Identification of the phenotypically normal, heterozygous (Wx/wx) genotype can only be done through molecular markers or by subsequent selfing and waxy screening of each plant, both of which processes are laborious and create additional effort in tracking, selfing, and identification of the waxy trait. This is followed by selfing and selection of elite inbreds that are homozygous for the waxy allele to yield the waxy homozygous elite converted line.

As an alternative to the waxy phenotype due to homozygosity for the naturally occurring wx allele, a dominant, heritable non-starchy ("pseudo-waxy") trait was created through suppression of the dominant Wx gene. The Wx-suppression transgene allows backcrossing and convenient selection of the waxy seed by visual inspection for direct advancement in the backcrossing and conversion process.

A vector (designated pMON81990) was designed to silence endogenous Wx transcripts, and contained a recombinant DNA construct including the rice actin promoter operably linked to a Wx-silencing sequence (i. e., DNA sequence for suppression of endogenous Wx mRNA transcripts), which in turn was linked to a PinII 3' UTR. The Wx-silencing sequence included a 1052-nucleotide suppression element having the sequence, ACCACGTCGGGGCCCTTCTGCTCTTCCAGCCTGCCGAT-GAACGCCACCAGCGGGATGTTCCGGTCCACCGGG-AGCCCGACCTCCGCCTGCAGCGCCTCCTTGTTCA-GCGCCTTGGCCTCCACGGCCGTCGACACGTCGTA-CTTCACGGCGATGTACTTGTCCCTGCTGGGGTCCC-ACTCGCTGACGTCCATGCCGTTGACGATGCCGGTG-ATGCCGGTGAGGCGCATGATGTTGTCGAGCTCGCA-GCCCCTGGCGATGCCGGAGATGAGCTCCTCGGCG-TAGTAGGGGCTGACGGTGAGGACCCTGTCGGCCT-CGAGGATCCCGGCCTTCATCCAGTTGATCTTCCGG-CCTTCCACGGGCTTCTCGTAGCCGTCGATGAAAT-CGAAGGACGACTTGAATCTCTCCGGGAGGTTCAG-CTCCGGGTAGTCGGAGAAGGCGAACCGGCCCTGG-TAGGAGATGTTGTGGATGCAGAAAGCGGTCTTTGC-GTCCCTGTAGATGCCGTGGGACTGGTAGTTGCTCTT-GAGGTAGCACGAGAGAGGGCCGGTGTGCCAGTCG-TTGCAGACGAACACGACGTCCTCCCCGTATGGTCC-GGAGAAGTATGGGTTGTTGTTGAGGCTCAGGATCC-TTGGAGCTT CAAGTGCTGCCTGGCAT<u>AGATTCAAG-TCGTCCTTCGATTTCATCGACGGCTACGAGAAGC-CCGTGGAAGGCCGGAAGATCAACTGGATGAAGGC-CGGGATCCTCGAGGCCGACAGGGTCCTCACCGTC-AGCCCCTACTACGCCGAGGAGCTCATCTCCGGCAT-CGCCAGGGGCTGCGAGCTCGACAACATCATGCGC-CTCACCGGCATCACCGGCATCGTCAACGGCATGG-ACGTCAGCGAGTGGGACCCCAGCAGGGACAAGT-ACATCGCCGTGAAGTACGACGTGTCGACGGCCGT-GGAGGCCAAGGCGCTGAACAAGGAGGCGCTGCA-GGCGGAGGTCGGGCTCCCGGTGGACCGGAACAT-CCCGCTGGTGGCGTTCATCGGCAGGCTGGAAGA-GCAGAAGGGCCCCGACGTTAG</u> (SEQ ID NO. 1). This Wx-silencing sequence includes an anti-sense segment (including nucleotides 4 through 651 of SEQ ID NO. 1) and a sense segment (including nucleotides 652 through 1052 of SEQ ID NO. 1) wherein the anti-sense segment and sense segment are not of equal length. Upon transcription of the Wx-silencing sequence to RNA, the resulting RNA sense segment hybridizes to its complementary sequence within the RNA anti-sense segment to form a double-stranded RNA "stem", the remaining (non-hybridized) portion of the RNA anti-sense segment serves as a single stranded RNA "loop" connecting the two strands of the "stem". The pMON81990 vector also included a 35S promoter operably linked to a selectable marker (nptII, encoding kanamycin resistance) and the Nos 3' UTR.

*Agrobacterium*-mediated transformation of the maize line LH244 with the pMON81990 vector resulted in transgenic plants. Samples of leaf tissue (V2 stage) from the transgenic plants were tested for copy number of the nptII gene or the PinII 3' UTR using the Taqman quantitative PCR system. Each of these transgenic events can serve as the at least one first parent plant of the invention, wherein the target RNA can be, e. g., the PinII 3' UTR (or alternatively, the Wx-silencing sequence).

Individual events carrying a single copy of the transgene were selected for starchy/non-starchy phenotype analysis by $I_2$/KI staining of mature pollen and endosperm. Plants in which Wx expression is transgenically suppressed were expected to show a non-starchy phenotype. A non-waxy phenotype was predicted in about 50% of pollen grains (which are haploid) from transgenic plants carrying a single copy of the DNA for suppressing expression of the endogenous Wx.

Mature pollen was collected at the time of pollen shed. Upon anther extrusion, tassels were lightly shaken to allow for fresh, live pollen to fall onto a microscope slide. Approximately 120 microliters of an $I_2$/KI solution was applied to and mixed with the pollen. A coverslip was applied and pollen color was observed under a dissecting microscope at approximately 10-50× magnification. An estimate of the percentage of blue-black staining pollen (starchy phenotype, indicative of non-suppressed Wx) as compared to the yellow/red staining pollen (non-starchy phenotype, indicative of wx or of suppressed Wx) was recorded along with photographs of the pollen. The results of the phenotypic analysis are given in Table 1. The majority of the transgenic events showed a reduced percentage of phenotypically starchy (staining blue-black) pollen grains. Pollen from non-transgenic plants (or from unrelated transgenic events) all or nearly all stained blue-black.

TABLE 1

| Event | NptII copy number | PinII 3' UTR expression | % starchy phenotype | Comments |
|---|---|---|---|---|
| ZM_M124897 | 1 | 3.0607 | 98 | |
| ZM_M124917 | 2 | 1.447 | 50 | many of the wx are intermediate |
| ZM_M124900 | 1 | | 90 | |
| ZM_M124904 | 1 | 0.0861 | 60 | Many of the wx are intermediate |
| ZM_M124907 | 2 | 0.5314 | 50 | some wx are intermediate |
| ZM_M124918 | 2 | 0.4198 | 100 | |
| ZM_M124910 | 0 | 0 | 98 | A few intermediate |
| ZM_M124899 | 1 | 0.477 | 70 | many of the wx are intermediate |
| ZM_M124896 | 1 | 3.3972 | 60 | many of the wx are intermediate |
| ZM_M126892 | 1 | 0.1488 | 50 | many wx intermediates |
| ZM_M124903 | 2 | 1.817 | 50 | all wx are intermediate |
| ZM_M124916 | 1 | 0.4187 | 60 | many of the wx are intermediate |
| ZM_M126880 | 1 | 0.3542 | 50 | few wx intermediates |
| ZM_M126872 | 1 | 0.2169 | 75 | all wx are intermediate |
| ZM_M124895 | | | 100 | |
| ZM_M126881 | 2 | 0.17 | 50 | 50% sterile pollen, plump pollen seg wx |
| ZM_M126875 | 2 | 0.2767 | 50 | some wx intermediates |
| ZM_M126884 | 2 | 0.0679 | 40 | |
| ZM_M126874 | 1 | 0.2004 | 50 | many wx intermediates |
| ZM_M126878 | 2 | 0.2518 | 50 | wx are very dark brown |
| ZM_M126883 | 1 | 0.1617 | 70 | many wx intermediates |
| ZM_M126873 | 1 | 0 | 90 | |
| ZM_M126891 | 1 | 0.0392 | 99 | some intermediate wx |
| ZM_M126893 | 2 | 0 | 100 | |
| ZM_M126886 | 1 | 0.1903 | 50 | some wx intermediates |
| ZM_M126878 | 2 | 0.2518 | 50 | wx are very dark brown |
| ZM_M126890 | 1 | 0.0315 | 50 | many wx intermediates |
| ZM_M126887 | 1 | 0.4924 | 100 | Different size pollen/ plant knotted |
| ZM_M126888 | 1 | 0.0001 | 95 | some wx intermediates |
| ZM_M126879 | 1 | 0.002 | 100 | |
| ZM_M128022 | 1 | | 100 | |
| ZM_M124905 | 1 | 0.0279 | 50 | all wx are intermediate |
| ZM_M126877 | 2 | 0.4706 | 50 | all wx are intermediate |
| ZM_M126876 | 1 | 0.0872 | 50 | many wx are intermediate |
| ZM_M129355 | 2 | 0.5267 | 50 | |
| ZM_M129355 | 2 | 0.5267 | 50 | |
| ZM_M129361 | 1 | 0.0156 | 50 | all wx are intermediate |

Figure 2:
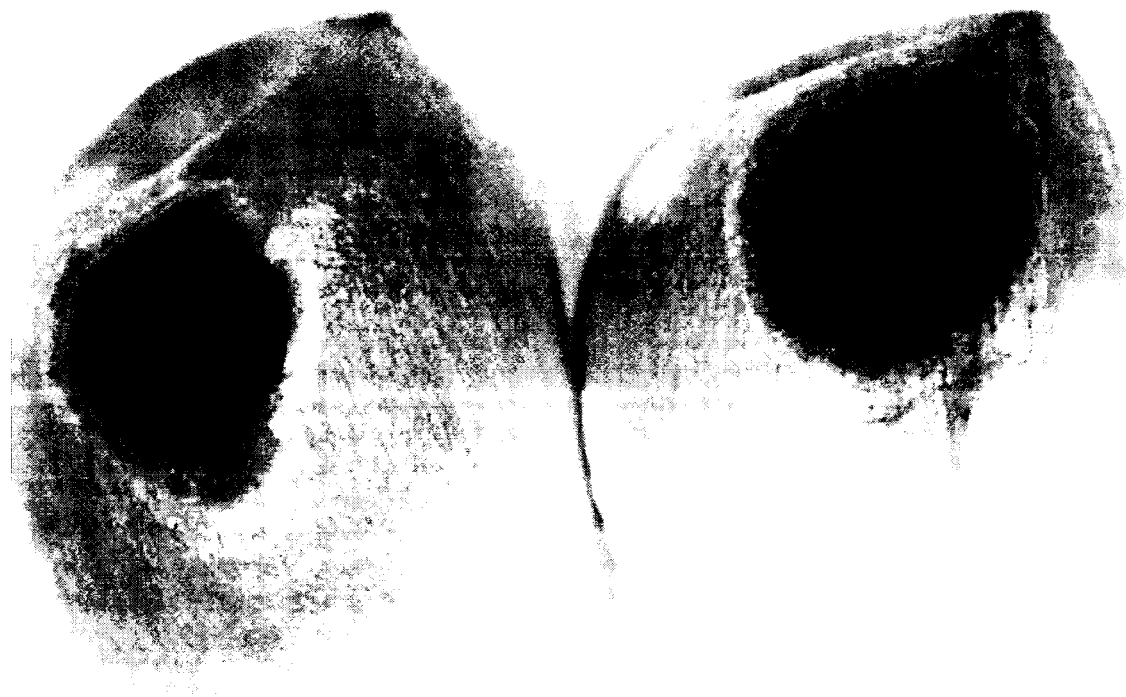
FIG. 2 depicts a photograph of the I₂/KI-stained endosperm in transgenic maize seed with a non-starchy ("waxy") phenotype (left) or a starchy phenotype (right), as described in Example 2.

Event ZM_M126880, which showed an approximately 50% starchy/50% non-starchy phenotype in the pollen, was self-pollinated, and the resulting kernels were stained to determine whether the Wx-silencing transgene was heritable as evidenced by a non-starchy phenotype in the endosperm tissue. A smooth incision into the endosperm of 15 randomly selected kernels was made with a scalpel. The $I_2KI$ solution was applied to the cut surface of kernels using a small paintbrush. Endosperm with a starchy phenotype (indicative of non-suppressed Wx) stained dark blue-black; endosperm with a non-starchy phenotype (indicative of wx or of suppressed Wx) stained reddish (FIG. 2). A non-starchy phenotype was observed in 13 of the 15 kernels, which approximated the expected phenotypic segregation ratio of 1:3.

Figure 3:
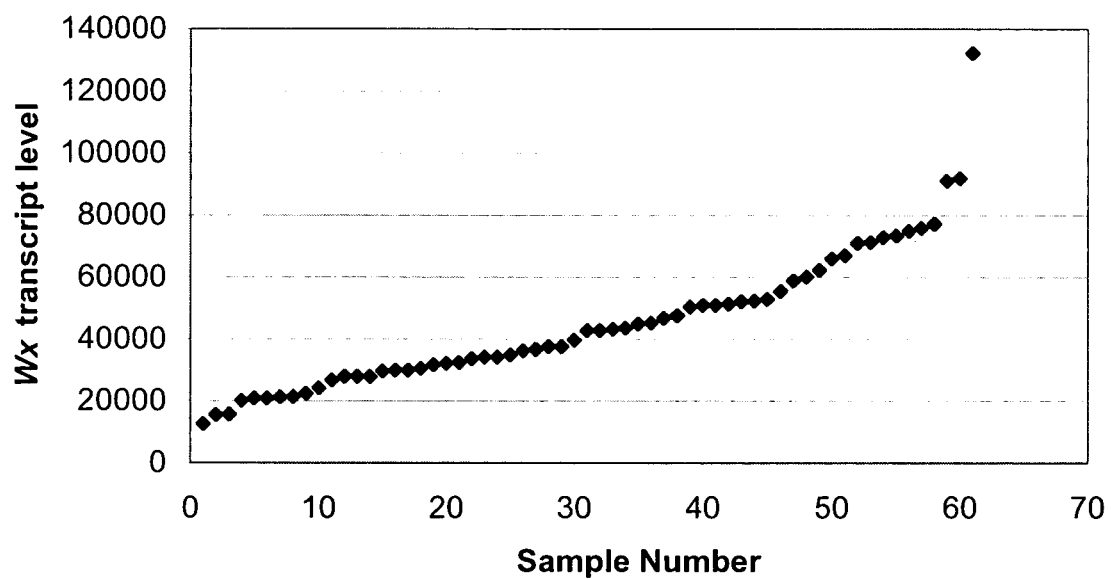
FIG. 3 depicts results from Taqman PCR quantitation of endogenous Wx transcript in a control transgenic event that lacked the Wx-silencing sequence, as described in Example 2.
Figure 4:
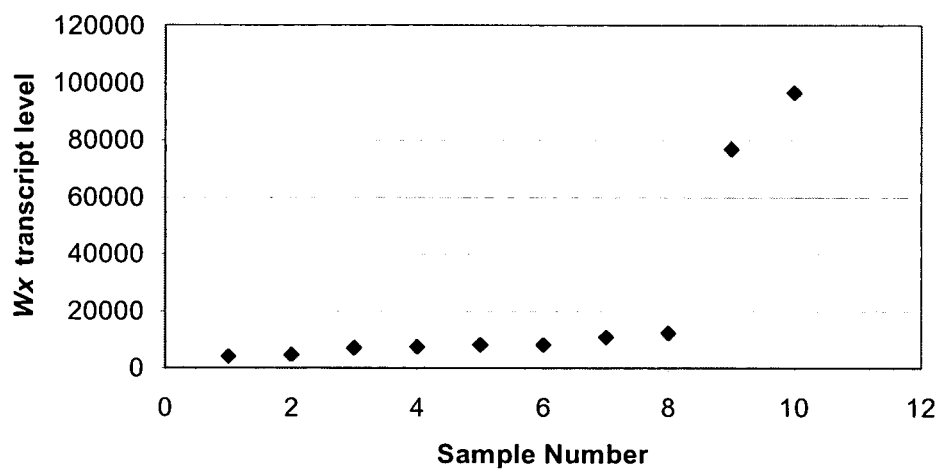
FIG. 4 depicts results from Taqman PCR quantitation of endogenous Wx transcript in the ZM_M126880 transgenic event that contained the Wx-silencing sequence, as described in Example 2.

The endogenous Wx transcript in the endosperm was quantified using Taqman PCR to determine if the observed non-starchy phenotype was due to suppression of the endogenous Wx transcript. Taqman analyses were performed on RNA extracted from the endosperm tissue of 61 individual kernels from a control transgenic event (pMON81999, which lacked the Wx-silencing sequence) to determine the range of endogenous Wx transcript levels. In the control event, endogenous Wx transcript levels generally ranged from about 20,000 to about 80,000 units (FIG. 3).

Ten kernels from the self-pollinated ear of event ZM_M126880 were randomly selected about 25-30 days after pollination. Endogenous Wx transcript levels were measured in the individual ZM_M126880 kernels. Eight out of ten kernels had endogenous Wx transcript levels of less than about 13,000 units, i. e., lower than the average level seen in the control (non-suppressed) transgenic event. Two of the ten kernels had endogenous Wx transcript levels of the same range (from about 80,000 to about 100,000 units) as the control transgenic event. The observed 8:2 ratio of low:high Wx transcript levels again approximated the expected phenotypic segregation ratio of 1:3. These data suggested that the pMON81990 construct suppressed the endogenous Wx transcripts, resulting in a non-starchy or pseudo-"waxy" phenotype that is heritable in a dominant fashion and thus particularly useful for breeding applications.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of providing plants with selective expression of an exogenous RNA, comprising:
   a) providing a set of first parent plants each expressing a recombinant DNA construct comprising a promoter operably linked to (i) DNA encoding an exogenous RNA, wherein said exogenous RNA is different for each of said first parent plants, and (ii) DNA encoding either a 5' UTR or a 3' UTR which is transcribed to a target RNA, wherein said target RNA is common to the set of first parent plants, and wherein said exogenous RNA and said target RNA are on the same RNA transcript;
   b) providing multiple second parent plants each expressing a recombinant DNA construct comprising a second promoter operably linked to DNA for suppressing expression of the target RNA, wherein each said second promoter is non-constitutive and is different for each of said multiple second parent plants;
   c) hybridizing said first parent plants and each of said multiple second parent plants to generate a heterogeneous population of hybrid progeny with regard to expression of said exogenous RNA; and
   d) producing a hybrid progeny with selective expression of said exogenous RNA relative to expression in said first parent plants.

2. The method of claim 1, wherein said DNA for suppressing is transcribed to double-stranded RNA.

3. The method of claim 1, wherein said exogenous RNA comprises:
   (a) coding RNA, or
   (b) non-coding RNA, or
   (c) both coding and non-coding RNA.

4. The method of claim 1, wherein said exogenous RNA comprises non-coding RNA selected from at least one of the group consisting of a promoter, a promoter enhancer element, a 3' untranslated region, a 5' untranslated region, a polyadenylation sequence, and an intron.

5. The method of claim 1, wherein said hybrid progeny comprises hybrid seed.

6. The method of claim 1, wherein said hybrid progeny comprises hybrid progeny plants.

7. The method of claim 1, wherein said second promoter is a spatially specific promoter, a temporally specific promoter, a developmentally specific promoter, or an inducible promoter.

8. A method of evaluating a constitutive, non-constitutive, spatial, temporal, developmental, or inducible expression pattern of an exogenous RNA in a plant, comprising:
   a) performing crosses of a set of first parent plants with multiple second parent plants, wherein each of said first parent plants expresses in its cells a recombinant DNA construct comprising a promoter operably linked to (i) DNA encoding an exogenous RNA, wherein said exogenous RNA is different for each of said first parent plants, and (ii) DNA encoding either a 5' UTR or a 3' UTR which is transcribed to a target RNA, wherein said target RNA is common to the set of first parent plants, and wherein said exogenous RNA and said target RNA are on the same RNA transcript, and each of said multiple second parent plants has in its genome a silencing sequence comprising a second promoter operably linked to DNA for suppressing expression of said target RNA, wherein each said second promoter is non-constitutive and is different for each of said multiple second parent plants, and said crosses result in the formation of a heterogeneous population of hybrid progeny; and b) evaluating said hybrid progeny for constitutive, non-constitutive, spatial, temporal, developmental, or inducible expression patterns of said exogenous RNA.

9. The method of claim 8, wherein said silencing is double-stranded RNA-mediated silencing.

10. The method of claim 8, wherein said exogenous RNA comprises:
(a) coding RNA, or
(b) non-coding RNA, or
(c) both coding and non-coding RNA.

11. The method of claim 8, wherein said exogenous RNA comprises non-coding RNA selected from at least one of the group consisting of a promoter, a promoter enhancer element, a 3' untranslated region, a 5' untranslated region, a polyadenylation sequence, and an intron.

12. The method of claim 8, wherein said hybrid progeny comprises hybrid seed.

13. The method of claim 8, wherein said hybrid progeny comprises hybrid progeny plants.

14. The method of claim 8, wherein said second promoter is a spatially specific promoter, a temporally specific promoter, a developmentally specific, or an inducible promoter.

* * * * *

SEQUENCE LISTING

```
<160> NUMBER OF SEQ ID NOS: 1

<210> SEQ ID NO 1
<211> LENGTH: 1052
<212> TYPE: DNA
<213> ORGANISM: Artificial Sequence
<220> FEATURE:
<223> OTHER INFORMATION: Synthetic construct

<400> SEQUENCE: 1
accacgtcgg ggcccttctg ctcttccagc ctgccgatga acgccaccag cgggatgttc      60
cggtccaccg ggagcccgac ctccgcctgc agcgcctcct tgttcagcgc cttggcctcc     120
acggccgtcg acacgtcgta cttcacggcg atgtacttgt ccctgctggg gtcccactcg     180
ctgacgtcca tgccgttgac gatgccggtg atgccggtga ggcgcatgat gttgtcgagc     240
tcgcagcccc tggcgatgcc ggagatgagc tcctcggcgt agtaggggct gacggtgagg     300
accctgtcgg cctcgaggat cccggccttc atccagttga tcttccggcc ttccacgggc     360
ttctcgtagc cgtcgatgaa atcgaaggac gacttgaatc tctccgggag gttcagctcc     420
gggtagtcgg agaaggcgaa ccggccctgg taggagatgt tgtggatgca gaaagcggtc     480
tttgcgtccc tgtagatgcc gtgggactgg tagttgctct tgaggtagca cgagagaggg     540
ccggtgtgcc agtcgttgca gacgaacacg acgtcctccc cgtatggtcc ggagaagtat     600
gggttgttgt tgaggctcag gatccttgga gcttcaagtg ctgcctggca tagattcaag     660
tcgtccttcg atttcatcga cggctacgag aagcccgtgg aaggccggaa gatcaactgg     720
atgaaggccg ggatcctcga ggccgacagg gtcctcaccg tcagcccta ctacgccgag      780 gagctcatct ccggcatcgc cagggctgc gagctcgaca acatcatgcg cctcaccggc      840
atcaccggca tcgtcaacgg catggacgtc agcgagtggg accccagcag ggacaagtac     900
atcgccgtga agtacgacgt gtcgacggcc gtggaggcca aggcgctgaa caaggaggcg     960
ctgcaggcgg aggtcgggct cccggtggac cggaacatcc cgctggtggc gttcatcggc    1020
aggctggaag agcagaaggg ccccgacgtt ag                                  1052
```